United States Patent [19]

Bagga

[11] Patent Number: 4,997,951
[45] Date of Patent: Mar. 5, 1991

[54] IMIDAZOLINE COMPOUNDS
[75] Inventor: Madan M. Bagga, Cambridge, England
[73] Assignee: Ciba-Geigy Corporation, Ardsley, N.Y.
[21] Appl. No.: 490,815
[22] Filed: Mar. 8, 1990
[30] Foreign Application Priority Data Mar. 17, 1989 [GB] United Kingdom ............ 89061980.)

[51] Int. Cl.$^5$ .......................................... C07D 233/22
[52] U.S. Cl. .................................................... 548/352
[58] Field of Search ......................................... 548/352
[56] References Cited

U.S. PATENT DOCUMENTS 2,888,458  5/1959  Stromberg ........................ 548/352
4,613,609  9/1986  Diamond et al. .................. 548/341

*Primary Examiner*—Mary C. Lee
*Assistant Examiner*—Lenora Miltenberger
*Attorney, Agent, or Firm*—JoAnn Villamizar

[57]  ABSTRACT

Imidazoline compounds of formula

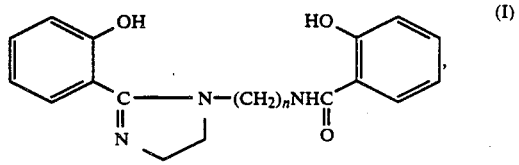

where n denotes 2 or 3, is suitable as cure accelerator in curable epoxide resin compositions comprising a latent curing agent.

4 Claims, No Drawings

IMIDAZOLINE COMPOUNDS

This invention relates to substituted imidazoline compounds useful in curable epoxide resin compositions, particularly composition for use as adhesives and sealants.

The sue of epoxide resins in adhesives and sealants has been commercial practice for several decades. Many hardeners for epoxide resins are reactive at room temperature and so need to be mixed with the epoxide just prior to use. Others are stable in admixture with the epoxide resin at room temperature, and harden only when heated to elevated temperatures. These hardeners, the so-called 'latent hardeners', or 'latent curing agents ', are available commercially and include dicyandiamide and polycarboxylic acid hydrazides.

Compositions containing an epoxide resin and such a latent hardener generally take about 15 minutes to 1 hour to cure at temperatures of about 180° C. Cure times can be shortened by incorporation of accelerators. An accelerator which is often used when compositions having good impact resistance and heat resistance are required, for example in certain adhesive pastes for the automotive industry, is benzimidazole. However, compositions containing benzimidazole as accelerator have undesirably limited storage stabilities at ambient temperatures.

It has now been found that when a novel substituted imidazoline obtainable by reaction of an ester of an aromatic hydroxy acid with diethylenetriamine is used as an accelerator in curable compositions containing an epoxide resin and dicyandiamide or a polycarboxylic acid hydrazide as latent curing agent, compositions can be obtained which have good impact resistance, good heat resistance and prolonged storage stability at ambient temperatures and can be cured rapidly at elevated temperatures.

Accordingly, the present invention provides imidazoline compounds of formula

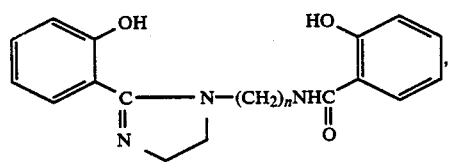

where n denotes 2 or 3.

Imidazoline compounds of formula I can be prepared by heating methyl salicylate with an amine of formula

NH$_2$CH$_2$CH$_2$NH(CH$_2$)$_n$NH$_2$   (II), where n is as hereinbefore defined, to give a compound of formula

and heating the compound of formula III to a higher temperature to effect elimination of water and thereby ring closure to give the desired imidazoline. The molor ratio of methyl salicylate to amind is usually at least 2:1, preferably from 3:1 to 4:1.

This preparation may be carried out with isolation of the intermediate compound of formula III or without such isolation, as desired. Thus, in one method, diethylenetriamine and the methyl ester of salicylic acid are heated at 80° to 110° C. to from a solid compound of formula III, which is filtered off from the reaction mixture, optionally using a liquid which does not dissolve the solid, e.g. acetone, as a diluent, dried and then heated at 140°–200° C. under vacuum to effect ring closure. In a second method, the diethylenetriamine and the methyl ester of salicylic acid are reacted at 80° to 110° C. to effect ring closure. In this second method, the triamine and ester may be dissolved in a solvent having a boiling point above 110° C., for example xylene or ethylene glycol, by means of which the ring closure reaction can be facilitated through azeotropic removal of water. Alternatively the reaction mixture may be refluxed to effect initial reaction and cyclisation in one step. The present invention also provides a curable composition comprising (A) an epoxide resin
(B) as latent curing agent for (A) ,dicyandiamide or a polycarboxylic acid, and
(C) as cure accelerator dispersed as a powder in the composition, an imidazoline of formula I as hereinbefore define.

Suitable epoxide resins (A), i.e. resins having, on average, more than one epoxide group per molecule, include those having, on average, more than one glycidyl group per molecular directly attached to an atom or atoms of oxygen, nitrogen, or sulphur.

As examples of such resins may be mentioned polyglycidyl esters obtainable by reaction of a compound containing two or more carboxylic acid groups per molecule with epichlorohydrin, glycerol dichlorohydrin, or beta-methylepichlorohydrin in the presence of an alkali. Such polyglycidyl esters may be derived from aliphatic carboxylic acids, e.g., oxalic acid, succinic acid, glutaric acid, adipic acid, pimelic acid, suberic acid, azelaic acid, sebacic acid, or dimerised or trimerixed linoleic acid; from cycloaliphatic polycarboxylic acids such as tetrahydrophthalic acid, 4, methyltetrahydrophthalic acid, hexahydrophthalic acid, and 4-methylhexahydrophthalic acid; and from aromatic polycarboxylic acids such as phthalic acid, isophthalic acid, and terephthalic acid.

Further examples are polyglycidyl ethers obtainable by reaction of a compound containing at least two free alcoholic hydroxyl and/or phenolic hydroxyl groups per molecule with the appropriate epichlorohydrin under alkaline conditions or, alternatively, in the presence of an acidic catalyst and subsequent treatment with alkali. These ethers may be made from acyclic alcohols such as ethylene glycol, diethylene glycol, and higher poly(oxyethylene)-glycols, propane-1,2-diol and poly-(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylolpropane, pentaerythritol, sorbitol, and polyepichlorohydrins; from cyclolaliphatic alcohols such as resorcitol, quinitol, bis(4-hydroxycyclohexyl)methane, 2,2-bis(4-hydroxycyclohexyl)-propane, and 1,1-bis(hydroxymethyl)-cyclohex-3-ene; and from alcohols having aromatic nuclei, such as N,N-bis(2-hydroxyethyl)-aniline and alcohols described in U.S. Pat. No. 4 284 574, such as 2,2-bis(p-3-ethoxy-2-hydroxypropyloxy)phenyl)propane, 2,2-bis(p-(3-butoxy-2-hydroxypropyloxy)-phenyl)propane, and bis(p-(3-butoxy-2-hydroxypropyloxy)-phenyl)sulphone. They may also made from mononuclear phenols, such as resorcinol and hydroquinone, and from polynuclear phenols, such as bis(4-hydroxyphenyl)methane, 4,4'-dihydroxydiphenyl, bis (4-hydroxyphenyl)sulphone, 1,1,2,2-tetrakis(4-hydroxyphenyl)ethane, 2,2-bis(4-hydroxyphenyl)propane, 2,2-bis(3,5-dibromo-4-hydroxyphenyl)propane, and novolaks formed from aldehydes, such as formaldehyde, acetaldehyde, chloral, and furfuraldehye, with phenols, such as phenol itself, and phenol substituted in the ring by chlorine atoms or by alkyl groups each containing up to nine carbon atoms, such as 4-chlorophenol, 2-methylphenol, and 4-tert.-butylpheol.

Poly(N-glycidy) compounds include, for example, those obtained by dehydrochlorination of the reaction products of epichlorohydrin with amines containing at least two aminohydrogen atoms, such as aniline, bis(4-aminophenyl)methane, m-xylylenediamine, and bis(4-methylaminophenyl)methane; triglycidy isocyanurate; and N,N'-diglycidyl derivatives of cyclid alkylene ureas, such as ethyleneurea and 1,3-propyleneurea, and of a hydantion such as 5,5-dimethylhydantion.

Examples of poly(S-glycidy) compounds are di-S-glycidyl derivatives of dithiols such as ethane-1,2-dithiol and bis(4-mercaptomethylphenyl) ether.

Epoxide resins having the glycidyl groups attached to different kinds of hetero atoms may be employed, e.g. the N,N,O- triglycidyl derivative of 4-aminophenol, the glycidyl etherglycidyl ester of salicyclic acid, N-glycidyl-N'-2-glycidyloxypropyl)-5,5-dimethylhydantion, and 2-glycidyloxy-1,3-bis(5,5-dimethyl-1-glycidylhydantion-3-yl)propane.

If desired, a mixture of epoxide resin may be used.

Preferred epoxide resins are liquids, and include polyglycidyl ethers, polyglycidyl esters, N,N'-diglycidylhydantions, and poly(N-glycidyl) derivatives of aromatic amins, Especially preferred resins arepolyglycidyl ethers of bisphenols, particulary 2,2-bis (4-hydroxyphenyl)propane(bisphenol A), and mixtures thereof with polyglycidyl ethers of polyhydric alcohols, particularly of butane-1,4-diol.

The latent curing agent (B) may be dicyandiamide or a hydrazide of a polycarboxylic acid. Suitable hydrazides include dihydrazides of aliphatic or aromatic dicarboxylic acids, such as stearic dihydrazide, adipic dihydrazide and isophthalic dihydrazide, with the last two being preferred.

The amount of latent curing agent (B) used in the compositon of the invention may be the amount conventionally used for the particular curing agent and epoxide resin. Such amounts are well known by those familiar with the formulation of curable epoxide resin compositions. When (B) is dicyandiamide the amount is generally within the range of 1 to 30, preferably 3 to 20, especially 5 to 10, parts by weight per 100 parts by weight of the epoxide resin (A). When (B) is a hydrazide of a polycarboxylic acid, the amount is generally such as to provide from 0.5 to 1.5, preferably 0.8 to 1.2, especially 0.9 to 1.1, active amino-hydrogen equivalents per epoxide equivalent of the epoxide resin (A).

The amount of the imidazoline accelerator (C) is not critical, provided an effective amount is present to give an accelerating effect. Generally, amounts within the range 0.1 to 20% preferably 1 to 10, especially 2 to 5%, by weight of the epoxide resin (A) are used.

The imidazoline accelerator (C) is generally ground to a fine powder, for example a powder having a particle size finer than 100 mesh (0.15 mm), before being mixed with the other components of the curable composition. Coarser particles of the imidazoline can usually be included in the composition since mixing of the components of the composition is conventionally carried out using conventional mixing equipment such as roll mills, which mixing can effect a reduction in the particle size.

The compositions of the invention may contain additives such as those conventionally incorporated in epoxide resin compositions in order to improve their physical or chemical properties in the cured or uncured state including, for example, pigments, dyes, flexibilisers, plasticisers, fillers, thixotropic agents and fire retardents. Suitable polymeric materials which can be added as toughening agents include acrylic esters of epoxide resins, polyurethane prepolymers, blocked polyisocyanates and elastomeric butadiene polymers.

An imidazoline of the invention is particularly useful in compositions of the invention which contain an elastomeric butadiene polymer as toughening agent. Such polymers include elastomeric copolymers of butadiene with acrylonitrile, preferably such copolymers having functional groups which are reactive with epoxide groups, e.g. hydroxyl, amine or, especially, carboxyl groups. Reactive functional group-containing copolymers of this type are available from Goodrich under the HYCAR trade mark. These reactive group-containing adducts are preferably incorporated in compositions of the invention as preformed adducts with epoxide resins such as those hereinbefore described. Preferred such adducts are epoxy-terminated adducts of a carboxyl-terminated acrylonitrilebutadiene copolymers with a polyglycidyl ether of a bisphenol, especially of bisphenol A. The toughening elastomeric polymer may be used in an amount up to 100% by weight of the epoxide resin (A).

As hereinbefore described, preferred epoxide resins (A) are liquid resins. Curable liquid compositions containing such resins may vary from unfilled compositions of low viscosity to pastes or putties which can contain large amounts of fillers or other additives. Compositions of the invention may also be in the form of films or sheets, which may be fibre-reinforced and may be supported on a carrier such as a glass fibre fabric.

Compositions of the invention can be cured by heating at elevated temperatures, generally from 140° to 220° C., preferably from 160° to 200° C. Cure can be effected in less than one minute, particularly at the higher temperatures within these ranges, but the heating can be continued, for example for up to 3 hours, to improve the physical properites of the cured product. When rapid heating is required, for example in the bonding or sealing of automobile components, this is conveniently achieved by the use of induction heating.

The curable compositions may be used as coating, casting or laminating resins or, more particularly, as adhesives or sealants.

The invention also provides a method of bonding or sealing two surfaces together which comprises applying a composition of the invention to one or both surfaces, placing the two surfaces together with the composition positioned therebetween and heating the resulting assembly until the composition is cured. This method may be used with surfaces of metal, such as steel or aluminium, plastic materials, glass, friction materials such as brake linings, and ceramic materials. It is particularly useful when both surfaces are of metal.

The invention is illustrated by the following Examples, in which parts and percentages are by weight unless otherwise indicated.

HYCAR CTBN 1300X13 used in the Examples is a carboxyl-terminated elastomeric copolymer of acrylonitrile and butadiene, available from the B. F. Goodrich Co., 6100 Oak Tree Boulevard, Cleveland, Ohio 44131 U.S.A.

EXAMPLE 1

Diethylenetriaminje (22.97 g; 0.22 mol) is added dropwise with stirring to methyl salicylate (102.6 g; 0.68 mol). The resulting mixture is heated under reflux for 6 hours, during which time a white solid is precipitated, and then cooled to 30° C. Acetone is added to dilute the mixture and the white solid is filtered off, washed in acetone and dried in a vacuum oven at 60° C. Elemental and spectral analysis of the intermediate product, which has a melting point of 150°-152° C., show it to be a compound of formula III where n denotes 2. (Analysis: Found C 63.48%, H 6.16%, N 12.39%; Theory C 62.95%, h 6.16%, N 12.24%.)

The intermediate is heated in a vacuum oven under a water pump vacuum at 160° C. for 90 minutes, crushed to a powder and then heated as before at 160° C. for a further hour. The resulting product, yield 47 g, has a melting point of 289°-291° C. Elemental and spectral analysis show it to be an imidaoline of formula I where n denotes 2.

Element Analysis: Found C 66.18%, H5.96%, N 12,87%; Theory C 66.46%, H 5,85%, N 12.92%.

$^1$H-NMR (acetic acid d$_4$): 6.6–7.7(m-8H), 4.3 (t-2H), 4.1 (t-2H), 3.7(s-4H)δ.

EXAMPLE 2

Diethylenetriamine (25.75g; 0.25 mol) is added dropwise with stirring to methyl salicylate (152 g; 1 mol). The mixture is heated under reflux for 2 hours (the initial reflux temperature of 105° c. gradually falling to 90° C), during which time a solid is precipitated. Methanol formed in the reaction is distilled off at atmospheric pressure, and the temperature of the reaction mixture is then allowed to rise to 170° C., where it is held for 2 hours. The reaction mixture is held at this temperature for a further 30 minutes under a reduced pressure of 400 mm Hg and then allowed to cool to 30° C. Acetone is added as a diluent to the resulting viscous mass, and the mixture is filtered to obtain the precipitated white solid. This solid is washed in acetone and dried in a vacuum oven at 60° C. Elemental and spectral analysis of the product, obtained in a yield of 31 g, show it to be the same as the product of Example 1.

EXAMPLE 3

N-(2-aminoethyle)-1,3-propane diamine (11.7 g; 0.10 mol) is added dropwise to a solution of methyl salicylate (30.4 g; 020 mol) in ethylene glycol (100 and then reluxed for 4 hours during which time a white solid precipitated. The mixture is cooled to 30° C. and filtered and washed in acetone and dried in a vacuum oven. Under these conditions the initial reaction and the final cyclisation occurs in one step. The resulting product, yield 13.8 g has a melting point of 280°-282° C. Elemental and spectral analysis show it to be the imidazoline of formula I in which n is 3.

Elemental analysis: Found C 66.27%, H 6.31%, N 12.26%; Theory C 67.26%, H 6.19% and N 12.39.

EXAMPLES 4–6

Curable paste compositions are prepared by dispersing a powdered hardener and the imidazoline of Example 1 (2 parts), together with highly dispersed silica (5 parts) as filler, in a liquid diglycidyl ether of bisphenol A having an epoxide content of 5.2 equivs/kg (100 parts). The gelation times of the compositions at particular temperatures are measured by placing a sample on a hot plate maintained at the test temperature and observing the time taken for gelation to occur. The storage lives of the compositions are determined by storing them in tubes in a fanned oven at 40° C., the end of the storage life being taken to be the time when the composition can no longer be spread at ambient temperature.

The nature and amount of the hardener in the compositions, together with the gel times and storage lives of the compositions, are given in the following table.

| Ex. | Hardener | Amount (parts) | Gel Time (min.) 160° C. | 180° C. | Storage Life |
|---|---|---|---|---|---|
| 4 | Dicyandiamide | 7.5 | 5.07 | 1.25 | Over 5 weeks |
| 5 | Adipic acid dihydrazide | 23.1 | 6.33 | 0.93 | Over 5 weeks |
| 6 | Isophthalic dihydrazide | 25.2 | 5.15 | 1.32 | Over 5 weeks |

EXAMPLE 7

The procedure of Examples 4 to 6 is repeated using a mixture of 80 parts of the diglycidyl ether used in those Examples and 20 parts of a liquid diglycidyl ether of butane-1,4diol having an epoxide content of 8,8 equivs/kg instead of the 100 of diglycidyl ether used in Examples 3–5, using dicyandiamide (8 parts) as hardener, and using 4 parts of the silica instead of the 5 parts used in Examples 3–5. The results are as follows:

| Gel Time (min.) | | Storage Life |
|---|---|---|
| 160° C. | 180° C. | |
| 2.31 | 0.68 | Over 15 weeks |

EXAMPLE 8

The procedure of Example 7 is repeated using the imidazoline of Example 3 instead of that of Example 1. The results are as follows:

| Gel Time (min.) | | Storage Life |
|---|---|---|
| 160° C. | 180° C. | |
| 2.98 | 0.75 | Over 15 weeks |

EXAMPLE 9

An adhesive composition is prepared containing

| | |
|---|---|
| Epoxide resin | 100 parts |
| Dicyandiamide | 7.5 parts |
| Highly dispersed silica | 5 parts |
| Glass microspheres | 1 part |
| Imidazoline of Formula II | 2 parts |

The epoxide resin used is a diglycidyl ether of bisphenol A having an epoxide content of 5.2 equiv./kg. The glass microspheres are incorporated to control glue line thickness.

This composition is applied to degreased, shot-blasted mild steel plates and lap joints are prepared having an overlap area of 645 mm². Cure is effected at 180° C. for 15 minutes, after which the joints are allowed to cool down to room temperature. The lap shear strength (average of 3 replicates) measured at a pulling rate of 7.5 mm/min. is 14.15 mPa.

EXAMPLE 10

Example 9 is repeated, replacing the composition used in that Example by a composition containing

| | |
|---|---|
| Epoxide resin used in Example 9 | 80 parts |
| Butane-1,4-diol diglycidyl ether | 20 parts |
| (epoxide content 8.8 equivs/kg) | |
| Dicyandiamide | 8 parts |
| Highly dispersed silica | 5 parts |
| Glass microspheres | 1 part |
| Imidazoline of Example 1 | 2 parts |

EXAMPLE 11

Example 9 is repeated, replacing the dicyandiamide used in that Example by adipic acid dihydrazide (23.1 parts). The average lap shear strength obtained is 11.29 MPa.

EXAMPLE 12

Example 9 is repeated, replacing the dicyandiamide by isophthalic acid dihydrazide (25.2 parts). The average lap shear strength obtained is 10.76 MPa.

EXAMPLE 13

An adhesive paste is prepared by dispersing dicyandiamide (9.5 parts), the imidazoline of Example 1 (1.8) and highly dispersed silica (6 parts) as filler in a mixture of a liquid diglycidyl ether of bisphenol A having an epoxide content of 5.4 equivs/kg (80 parts) and an adduct of this diglycidyl ether with an equal amount of HYCAR CTBN 1300X13 (prepared by heating the materials together at 150° C. for 2 hours), the adduct having an epoxide content of 2.4 equivs/kg (35 parts). A thin film of this paste is spread on a tinplate foil coated with a release agent. The film is cured by heating at 190° C. for 15 minutes and then peeled off for thermomechanical analysis to determine the heat resistance of the cured composition. On testing the cured film in a Perkin-Elmer thermomechanical analyser, model TMS 2, using a probe of 0.62 mm diameter under a load of 100 g and a scan rate of 10° C./min., onset of penetration occurs at 130.6° C.

I claim:

1. An imidazoline compound of formula

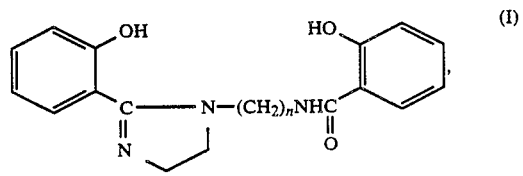

where n is 2 or 3.

2. A method of preparing imidazoline compounds of formula I according to claim 1, which comprises heating methyl salicylate with an amine of formula

where n is 2 or 3, to give a compound of formula

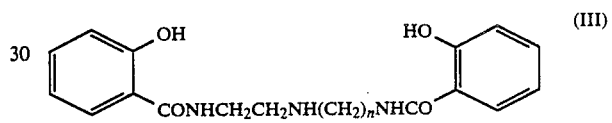

and heating the compound of formula III to effect elimination of water and thereby ring closure to give the desired imidazoline.

3. A method of preparing imidazoline compounds according to claim 2, which comprises heating in a solvent under reflux methyl salicylate and an amine of formula

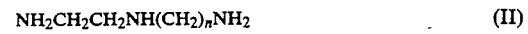

until the imidazoline is formed.

4. A method according to claim 2 in which the molar ratio of methyl salicylate to amine is from 3:1 to 4:1.

* * * * *